US006043396A

United States Patent [19]
Stürmer et al.

[11] Patent Number: 6,043,396
[45] Date of Patent: Mar. 28, 2000

[54] PREPARATION OF OPTICALLY ACTIVE PHOSPHOLANES, THEIR METAL COMPLEXES AND USE IN ASYMMETRIC SYNTHESIS

[75] Inventors: Rainer Stürmer, Rödersheim-Gronau; Armin Börner, Rostock; Jens Holz, Rostock; Gudrun Voss, Rostock, all of Germany

[73] Assignee: BASF Aktiengesellschaft, Ludwigshafen, Germany

[21] Appl. No.: 09/092,970

[22] Filed: Jun. 8, 1998

[30] Foreign Application Priority Data

Jun. 18, 1997 [DE] Germany .................. 197 25 796

[51] Int. Cl.[7] ........................................ C07F 9/02
[52] U.S. Cl. .................................. 568/12; 568/17
[58] Field of Search .................. 568/12, 17; 560/18

[56] References Cited

U.S. PATENT DOCUMENTS 5,171,892  12/1992  Burk ............................... 568/12

FOREIGN PATENT DOCUMENTS

| | | |
|---|---|---|
| 151 282 | 8/1985 | European Pat. Off. . |
| 158 875 | 10/1985 | European Pat. Off. . |
| 185 882 | 7/1986 | European Pat. Off. . |
| 271 311 | 6/1988 | European Pat. Off. . |
| 437 690 | 7/1991 | European Pat. Off. . |
| 614 901 | 9/1994 | European Pat. Off. . |
| 91/17998 | 11/1991 | WIPO . |
| 92/19636 | 11/1992 | WIPO . |

OTHER PUBLICATIONS

Carmichael et al., "Hybrid P–chiral diphosphines for asymmetric hydrogenation", Chem. Commun., pp. 261–262, 1999.
Holz et al., "Synthesis of a New Class of Functionalized Chiral Bisphospholane Ligands and the Application in Enantioselective Hydrogenations", J. Org. Chem., vol. 63: 8031–8034, 1998.
Genet et al., "New Developments in Chiral Ruthenium (II) Catalysts for Aymmetric Hydrogenation and Synthetic Applications", ACS Sympos. Ser. 641 (Reductions in Organic Synthesis), pp. 31–51, 1996.
Burk et al., "Asymmetric catalytic routes to chiral building blocks of medicinal interest", Pure & Appl. Chem., vol. 68(1): 37–44, 1996.
Brunner et al., "Enantioselektive Katalysen. LIX. Addition von optisch aktiven P–H Verbindungen an P–substutierte Olefine", Journal of Organometallic Chemistry, vol. 413: 55–63, 1991.

Brunner et al., "Optisch aktive Ubergangsmetallkomplexe.", Journal of Organometallic Chemistry, vol. 393: 401–409 & 411–422, 1990.
Brunner et al., "Asymmetric Catalyses. XXXIII. New Optically Active Phospholanes Derived From Tartaric Acid.", Journal of Organometallic Chemistry, vol. 328: 71–80, 1987.
J. Am. Chem. Soc., 1996, 118, 5142–5143, Burk et al.
Inorganica Chim. Acta, 73 (1983) 275–279, Uson et al.
J. Am. Chem. Soc., 1995, 117, 9375–9376, Burk et al.
J. Am. Chem. Soc., 1993, 115, 10125–10138, Burk et al.
J. Am. Chem. soc. 1991, 113, 8519–8521, Burk.
Tetrahedron: Asymmetry vol. 2, No. 7, pp 569–592, 1991, Burk et al.
Asymmetric Synthesis, vol. 5 chiral Catalyst, 1985, pp. 12–23.
Acc. Chem. Res. 1990, 23, 345–350, Noyori et al.
J. Am. Chem. Soc. 1984, 5208–5217, Tani et al.
Asymmetric catalyses, Jrl. Org. Chem. 328 (1987) 71–80, Brunner et al.

*Primary Examiner*—Howard C. Lee
*Attorney, Agent, or Firm*—Keil & Weinkauf

[57] ABSTRACT

Phospholanes and diphospholanes of the formula I

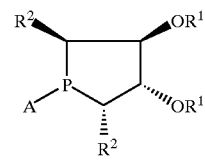

where:

R[1] and R[2] are, independently of one another, $C_1$–$C_6$-alkyl, aryl, alkylaryl, R[1] is also hydrogen, A is either R[1] or

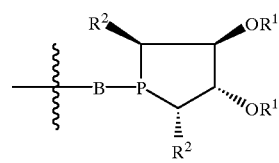

B is a linker having 1–5 carbon atoms between the two phosphorus atoms, and their use as catalyst in asymmetric synthesis.

10 Claims, No Drawings

PREPARATION OF OPTICALLY ACTIVE PHOSPHOLANES, THEIR METAL COMPLEXES AND USE IN ASYMMETRIC SYNTHESIS

The invention describes novel optically active phospholanes and bisphospholanes, their preparation and use as ligands in metal complexes, and the use of the metal complexes for enantioselective synthesis.

Enantioselective hydrogenation and isomerization with rhodium and ruthenium complexes is of great importance for synthesizing optically active compounds (eg. Tani et al. J. Am. Chem. Soc. 106 (1984) 5211; R. Noyori, Acc. Chem. Res. 23 (1990) 345). The stoichiometric starting material hydrogen is not costly, but the catalysts used, which are mostly prepared from an optically active diphosphine ligand and a rhodium or ruthenium compound, are very costly and obtainable only in a complicated way.

The known methods for preparing optically active phosphines and diphosphines are uniformly complicated and mostly include a technically elaborate and costly racemate resolution (eg. EP-A 0614901; EP-A 0271311; H. B. Kagan, "Chiral Ligands for Asymmetric Catalysis" in Asymmetric Synthesis 5 (1985) 13–23, EP-A 0151282; EP-A 0185882; R. Noyori, Acc. Chem. Res. 23 (1990) 345; EP-269395; M. J. Burk, Tetrahedron Asymmetry (1991) 569–592; J. Am. Chem. Soc. 113 (1991) 8518–9, ibid. 115 (1993) 10125–138, ibid. 117 (1995) 9375–76, ibid 118 (1996) 5142. These disadvantages make industrial use difficult and uneconomic.

It is an object of the present invention to provide phosphine ligands which can be prepared easily and at low cost and which are good ligands for metal complex catalysts for enantioselective synthesis.

We have found that this object is achieved by a particularly efficient class of ligands, namely phospholanes obtainable from the chiral pool (2). The starting material in this case is mannitol and other carbohydrates, which are available at low cost and in large quantity.

The resulting phospholanes and diphospholanes provide excellent enantiomeric excesses in asymmetric hydrogenations. The known DUPHOS ligands of Burk et al. (M. J. Burk, Tetrahedron Asymmetry (1991) 569–592; J. Am. Chem. Soc. 113 (1991) 8518–9, ibid. 115 (1993) 10125–138, ibid. 117 (1995) 9375–76, ibid. 118 (1996) 5142) are, in contrast to the present invention, much more complicated to synthesize. Synthesis of the DUPHOS ligands requires, inter alia, an impracticable electrolytic Kolbe synthesis plus an asymmetric hydrogenation.

The present invention avoids these difficulties by using the sugar mannitol which is available enantiomerically pure from natural sources. In addition, this starting material opens up a route to structural analogs substituted in the 3 and 4 positions of the phospholane ring, ie. to analogs which cannot be prepared by the known DUPHOS synthesis.

The invention relates to phospholanes and diphospholanes of the formula I

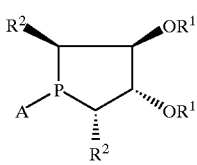

I where $R^1$ and $R^2$ are, independently of one another, $C_1$–$C_6$-alkyl, aryl, alkylaryl, $R^1$ is also hydrogen, A is either $R^1$ or

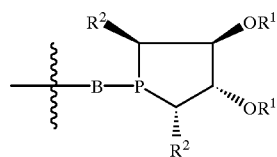

B is a linker having 1–5 carbon atoms between the two phosphorus atoms.

Preferred substituents $R^1$ and $R^2$ are methyl, ethyl, n-propyl, isopropyl, n-butyl, isobutyl, tert-butyl, benzyl.

Furthermore, also those radicals $R^1$ where the two $R_1$ radicals together mean isopropylidene or benzylidene.

Preferred diphospholanes are those where

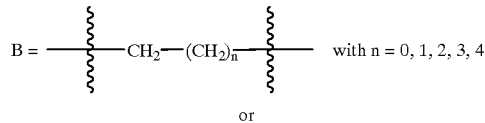

with n = 0, 1, 2, 3, 4 or

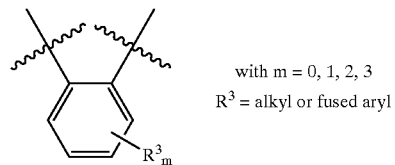

with m = 0, 1, 2, 3
$R^3$ = alkyl or fused aryl

Particularly preferred linkers B are those where n is 1 or 2 or m is 0.

The invention furthermore relates to metal complexes comprising the abovementioned phospholanes.

Particularly preferred metal complexes are those which contain ruthenium or rhodium as central atom. These complexes can be prepared by synthesizing in a known manner (eg. Uson, Inorg. Chim. Acta 73 (1983) 275, EP-A 0158875, EP-A 437690) catalytically active complexes by reaction with rhodium, iridium, ruthenium, palladium, platinum or nickel complexes which contain labile ligands (eg. [RuCl$_2$(COD)]n, Rh(COD)$_2$BF$_4$, Rh(COD)$_2$ClO$_4$, [Ir(COD)Cl]$_2$, p-cymene-ruthenium chloride dimer).

The invention furthermore relates to the use of these metal complexes in asymmetric synthesis, in particular as catalyst for hydrogenations, hydroformylations, hydrocyanations, allylic substitutions and isomerizations of allylamines to enamines.

These reactions can be carried out with the novel metal complexes under conditions familiar to the skilled worker.

Hydrogenation with the novel metal complexes is, as a rule, carried out at from –20 to 150° C., preferably at 0 to 100° C., and particularly preferably at 15–40° C.

The hydrogen pressure can vary within a wide range from 0.1 bar to 300 bar for the novel hydrogenation process. Very good results are obtained in a pressure range of 1–10, preferably 1–2, bar.

It is a particular advantage with the novel ligands that the hydrogenations can be carried out very efficiently at the low hydrogen pressure of 1–2 bar.

EXAMPLE 1
Preparation of Tetrabenzyloxy-Me-DUPHOS 1,2;5,6-Di-O-isopropylidene-D-mannitol (1): commercially obtainable from FLUKA (order no. 38410).

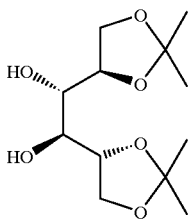

3,4-Di-O-benzyl-1,2;5,6-di-O-isopropylidene-D-mannitol (2): prepared as described by J. Jurcak, T. Bauer, M. Chmielewski, *Carbohydr. Res.* 164 (1987) 493.

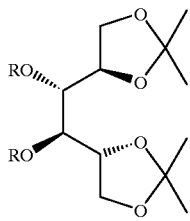

3,4-Di-O-benzyl-D-mannitol (3): prepared as described by J. Jurcak, T. Bauer, M. Chmielewski, *Carbohydr. Res.* 164 (1987) 493.

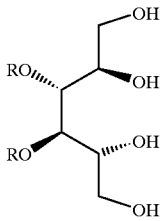

3,4-Di-O-benzyl-1,6-di-O-toluolsulfonyl-D-mannitol (4): prepared as described by J. Fittremann, A. Dureault, J.-C. Depezay, *Tetrahedron Letters* 35 (1994) 1201.

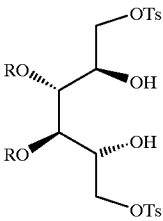

(2R,3R,4R,5R)-3,4-Dibenzyloxy-2,5-hexanediol (5): A solution consisting of 10 g (14.9 mmol) of the ditosylate 4 in 30 ml of THF is slowly added dropwise to a suspension of 2.25 g (59.6 mmol) of LiAlH₄ in 100 ml of THF at room temperature. After stirring the suspension for one hour, it is refluxed for two hours. After cooling, the hydride is decomposed by cautious addition in succession of 2.25 ml of water, 2.25 ml of 15% strength NaOH and a further 6.75 ml of water. The solution is filtered off from the precipitated inorganic compounds, and this residue is extracted with methylene chloride in a Soxhlet. The combined solutions are dried and the residue after removal of the solvents by distillation is purified by column chromatography (n-hexane:AcOEt=1:2; $R_f$=0.45). Yield: 3.6 g (73%), white solid, melting point 46–50° C. $[\alpha]^{26}_D$=–4.7 (c 0.990, CHCl₃), ¹H-NMR (CDCl₃): 7.40–7.25 (10H, m, arom. H), 4.65 (4H, AB sp., CH₂Ph, $^2J_{A,B}$=11.3 Hz), 4.09 (2H, m, H-2+H-5), 3.53 (2H, m, H-3+H-4), 2.96 (2H, s (Br), 2×OH), 1.25 (6H, d, 2×CH₃, $^3J_{H,H}$=6.4 Hz); ¹³C-NMR (CDCl₃): 137.4, 128.5, 128.2, 128.0 (arom. C), 81.5 (C-3+C-4), 73.3 (2×CH₂Ph), 67.3 (C-2+C-5), 19.7 (2×CH₃); IR (KBr): 3417, 3287, 3031, 2987, 2965, 2934, 2882, 1455, 1316, 1210, 1112, 1092, 1075, 1056, 1028, 764, 726, 697; MS (70 eV, m/z): 331 [M⁺+H] (1), 297 [M⁺—CH₃—H₂O] (1), 285 [M—C₂H₅O] (2); C₂₀H₂₆O₄ (330.43) calculated: C: 72.70% H: 7.93% found: C; 72.79% H: 7.94%;

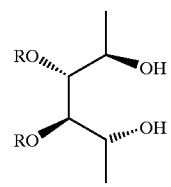

(4R,5R,6R,7R)-5,6-Dibenzyloxy-4,7-dimethyl[1,3,2] dioxathiepane 2,2-dioxide (6): 4.75 g (14.4 mmol) of the diol 5 are refluxed with 1.3 ml of thionyl chloride in 20 ml of tetrachloromethane for 1.5 h. After cooling, the solvent is removed in a rotary evaporator, and the resulting residue is taken up in 10 ml of tetrachloromethane, 10 ml of acetonitrile and 15 ml of water. The solution is cooled to 0° C. and 0.021 g (0.08 mmol) of RuCl₃*3H₂O is added, followed by 6.2 g (29.0 mmol) of sodium periodate. After the solution has been stirred at room temperature for one hour, 75 ml of water are added, followed by extraction with 4×100 ml of diethyl ether. The combined extracts are washed once with saturated NaCl solution and then dried with Na₂SO₄ and filtered through kieselguhr. The ethereal solution is concentrated, and the cyclic sulfate 6 is purified by column chromatography (n-hexane : AcOEt=9:1, $R_f$=0.25).

Yield 3.4 g (60%) white crystals. Melting point 90–94° C. $[\alpha]^{23}_D$=–2.8 (c 1.012, CHCl₃). ¹H-NMR (CDCl₃): 7.40–7.25 (10H, m, arom. H), 4.79 (4H, AB sp., CH₂Ph, $^2J_{A,B}$=10.8 Hz), 4.09 (2H, m, H-2+H-5), 3.55 (2H, m, H-3+H-4), 1.53 (6H, d, 2×CH₃, $^3J_{H,H}$=6.4Hz); ¹³C-NMR (CDCl₃): 137.1, 128.6, 128.1, 127.7 (arom. C), 84.2 (C-3+C-4), 79.4 (C-2+C-5), 76.2 (2×CH₂Ph), 17.9 (2×CH₃); IR (KBr): 3090, 3062, 3027, 2989, 2939, 2881, 2861, 1498, 1453, 1395, 1380, 1349, 1208, 1103, 1071, 1020, 949, 899, 841, 750, 741, 703, 699, 611; MS (70 eV, m/z): 392 [M⁺¹ (1), 301 [M⁺—C₇H₇] (47), 195 [M⁺—C₇H₇—C₇H₆O] (36), 91 [C₇H₇⁺] (100); C₂₀H₂₄O₆S (392.47) calculated: C: 61.21% H: 6.16% S: 8.17%; found: C: 61.20% H: 6.24% S: 8.08%;

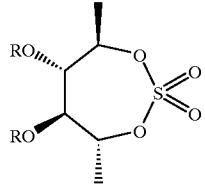

1,2-Bis((2S,3S,4S,5S)-5,6-dibenzyloxy-4,7-dimethylphospholanyl)benzene (7): 4.95 ml (7.93 mmol) of n-BuLi (1.6 M in hexane) are added dropwise to a solution of 0.564 g (3.96 mmol) of 1,2-bis(phosphinyl)benzene in 70 ml of THF at room temperature. The resulting clear yellow solution is stirred for a further 2 hours and then a solution of 3.11 g (7.92 mmol) of the cyclic sulfate 6 in 15 ml of THF is slowly added. This results in the color changing to reddish orange. After four hours, a further 5.45 ml (8.71 mmol) of n-BuLi are introduced into the reaction mixture, which is left to stir at room temperature for a further 16 h. For workup, 3 ml of methanol are added to the resulting red solution, and the THF is removed under reduced pressure. The residue is taken up in 50 ml of methylene chloride and washed with water (20 ml) under anaerobic conditions. Drying ($Na_2SO_4$) and removal of the solvent are followed by purification by chromatography (n-hexane: AcOEt=9:1, $R_f$=0.2).

42% yield of colorless syrup. $^1$H-NMR ($C_6D_6$): 7.70–7.00 (10H, m, arom. H), 4.50 (8H, m, 4×$CH_2$Ph), 4.05–3.93 (4H, m, H-2+H-5), 3.15–2.94 (4H, m, H-2+H-5), 1.47 (6H, m, $CH_3$), 0.88 (6H, m, $CH_3$); $^{13}$C-NMR ($C_6D_6$): 143.3 (m), 139.3, 139.3, 128.5–127.5 (arom. C), 85.2+84.2 (C-3+C-4), 72.2+72.0 (4×$CH_2$Ph), 32.4 (m, C-2+C-5), 14.5 ($CH_3$), 13.4 ($CH_3$); $^{31}$P-NMR ($C_6D_6$): −3.4; MS ($FD_{pos}$): 731 [$M^+$+H] (100);

(COD)Rh(1,2-Bis((2S,3S,4S,5S)-5,6-dibenzyloxy-4,7-dimethylphospholanyl)benzene (8): One equivalent (167 mg) of [$RH(COD)_2$]$BF_4$ is added to a solution of 300 mg (0.41 mmol) of the phospholane 7 in 3 ml of THF, and the mixture is stirred at room temperature for one hour. 20 ml of diethyl ether are then added to the solution, whereupon a dark brown oil separates out. After removal of the supernatant solution, the residue is washed with diethyl ether (3×10 ml) and then dried under reduced pressure. This results in the required complex as a brown powder.

Yield 200 mg (47%). $^1$H-NMR ($CHCl_3$): 7.70–7.00 (10H, m, arom. H), 4.50 (8H, m, 4×$CH_2$Ph), 4.05–3.93 (4H, m, H-2+H-5), 3.15–2.94 (4H, m, H-2+H-5), 1.47 (6H, m, $CH_3$), 0.88 (6H, m, $CH_3$); $^{13}$C-NMR ($C_6D_6$): 143.3 (m), 139.3, 139.3, 128.5–127.5 (arom. C), 85.2+84.2 (C-3+C-4), 72.2+72.0 (4×$CH_2$Ph), 32.4 (m, C-2+C-5), 14.5 ($CH_3$), 13.4 ($CH_3$); $^{31}$P-NMR ($CDCl_3$): 76.1 (d, $^1J_{Rh,P}$=152.6 Hz); MS ($FD_{pos}$): 941 [$M^{+\leftarrow BF}{}_4$] (100);

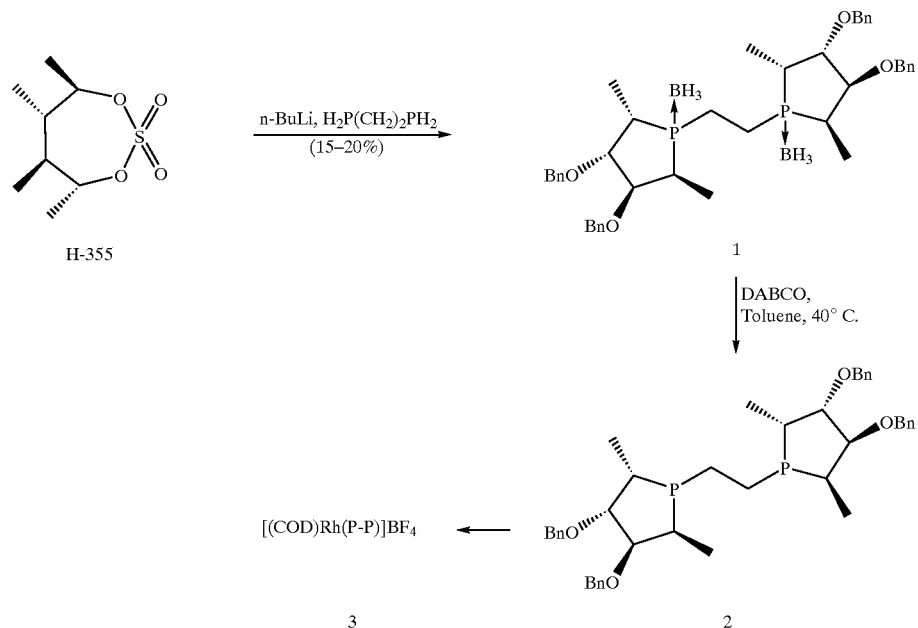

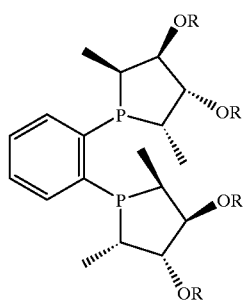

1,2-Bis((2S,3S,4S, 5S)-5,6-dibenzyloxy-4,7-dimethylphospholanyl)ethane (borane complex) (1): 5.26 ml. (8.42 mmol) of n-BuLi (1.6 M in hexane) are added dropwise to a stirred solution of 0.396 g (4.21 mmol) of 1,2-bis(phosphanyl)ethane in 70 ml of THF at room temperature. The resulting clear yellow solution is stirred for a further 2 hours and then a solution of 3.30 g (7.92 mmol) of the cyclic sulfate ((4R,5R,6R,7R)-5,6-dibenzyloxy-4,7-dimethyl[1,3,2]dioxathiepane 2,2-dioxide) dissolved in 15 ml of THF is slowly added. This results in the color changing to yellowish brown. After four hours, a further 5.79 ml (9.26 mmol) of n-BuLi (1.6 M) are introduced into the reaction mixture, which is left to stir at room temperature for 16 hours. For workup, the resulting clear pale brown solution is cooled to 0° C. and 2.2 eq of $BH_3$-THF complex (1 M, 9.26 ml) are added. After 2 hours, the solvent is removed, the residue is taken up in 20 ml of water, and the product is extracted with methylene chloride (3×30 ml).

After concentration, the required product is obtained by purification by column chromatography (n-hexane:AcOEt=4:1, $R_f$=0.25) in a yield of 480 mg (16%). $^1$H-NMR (CDCl$_3$): 7.38–7.20 (20H, m, arom. H), 4.54–4.39 (8H, m, 4×CH$_2$Ph), 3.92–3.84 (4H, m, CH—O), 2.55 (2H, m, CH—P), 2.24 (2H, m, CH—P), 2.00–1.64 (4H, m, (CH$_2$)$_2$), 1.26–1.10 (12H, m, CH$_3$), 0.90–0.05 (6H, broad, BH$_3$); $^{13}$C-NMR (CDCl$_3$): 137.8, 137.5, 128.5–127.4 (arom. C), 84.0+82.3 (C-3+C-4), 72.5+72.3 (CH$_2$Ph), 34.3 (m, C-2+C-5), 17.8 (CH$_2$)$_2$, 10 (CH$_3$), 8.1 (CH$_3$); $^{31}$P-NMR (CDCl$_3$): 39.1;

1,2-Bis((2S,3S,4S,5S)-5,6-dibenzyloxy-4,7-dimethylphospholanyl)ethane (2): 290 mg (0.41 mmol) of compound 1 are stirred with 3 eq of DABCO in 15 ml of toluene at 40° C. After conversion is shown to be complete in the TLC (n-hexane:AcOEt=4:1, $R_f$=0.3), compound 2 is obtained after workup by column chromatography in a yield of 75% (210 mg). $^1$H-NMR (CDCl$_3$): 7.40–7.10 (20H, m, arom. H), 4.54–4.34 (8H, m, 4×CH$_2$Ph), 3.96–3.78 (4H, m, CH—O), 2.53 (2H, m, CH—P), 2.10 (2H, m, CH—P), 1.73–1.50 (4H, m, (CH$_2$)$_2$), 1.30–1.05 (12H, m, CH$_3$); $^{13}$C-NMR (CDCl$_3$): 138.7, 138.5, 128.3–127.3 (arom. C), 86.8+85.1 (C-3+C-4), 72.2+71.9 (CH$_2$Ph), 33.5 (m, C-2+C-5), 22.6 (CH$_2$)$_2$, 14.1 (CH$_3$), 9.4 (CH$_3$); $^{31}$P-NMR (CDCl$_3$): −1.5;

Rh[1,2-Bis((2S,3S,4S,5S)-5,6-dibenzyloxy-4,7-dimethyl-phospholanyl)ethane][COD] tetrafluoroborate (3): One equivalent (107 mg) of [Rh(COD)$_2$]BF$_4$ is added to a solution of 180 mg (0.26 mmol) of the bisphospholane 2 in 3 ml of THF, and the mixture is stirred at room temperature for one hour. 15 ml of diethyl ether are then added to the solution, whereupon a dark brown oil separates out. After removal of the supernatant solution, the viscous residue is washed with diethyl ether (3×10 ml), whereupon a solid precipitate forms. It is then dried in vacuo. This results in the required complex as an orange-brown powder in a yield of 134 mg (52%). $^1$H-NMR (CHCl$_3$): 7.40–7.10 (20H, m, arom. H), 5.27 (2H, m, CH(COD)), 5.14 (2H, m, CH(COD)), 4.58–4.40 (8H, m, 4×CH$_2$Ph), 4.10–3.93 (4H, m, H-2+H-5), remainder not analyzable; $^{13}$C-NMR (CDCl$_3$): 137.6, 137.2, 128.7–127.5 (arom. C), 101.8 (m, COD), 95.5 (m, COD), 83.8+83.5 (C-3+C-4), 73.0+72.6 (4×CH$_2$Ph), 41.9+33.5 (m, C-2+C-5), 14.5 (CH$_3$), 13.4 (CH$_3$); $^{31}$P-NMR (CDCl$_3$): 72.7 (d, $^2J_{Rh,P}$=150 Hz);

EXAMPLE 2

Typical Method for Asymmetric Hydrogenation 10 mmol of substrate are added to 0.01 mmol of the catalyst in MeOH under protective gas in a Roth laboratory autoclave, and hydrogenation is carried out with a hydrogen pressure of 1 bar at room temperature. The results and hydrogenation times are evident from the following table.

Hydrogenation Results

Conditions

25° C., 1 bar H$_2$, 10 mmol substrate, 0.01 mol % Rh catalyst (8) of Example 1, MeOH

| Substrate | Time for 100% conversion | ee (abs. config) | Product |
|---|---|---|---|
| PhCH=C(NHAc)COOH | 55 | 95 (S) | PhCH$_2$CH(NHAc)COOH |
| PhCH=C(NHAc)COOMe | 75 | 92.5 (S) | PhCH$_2$CH(NHAc)COOMe |
| HOOC-C(=CH$_2$)-COOH | 10 | 98 (R) | HOOC-CH(CH$_3$)-COOH |
| MeOOC-C(=CH$_2$)-COOMe | 30 | 98 (R) | MeOOC-CH(CH$_3$)-COOMe |

Analyses

Hydrogenation of the prochiral acids AH and ItH2 was followed by esterification of a small amount (about 1 ml of solution) with diazomethane or trimethylsilyldiazomethane. The methyl esters which were then available from all the hydrogenation reactions were analyzed as follows:
AH/AMe: Methyl (R/S)-2-acetylamino-3-phenylpropionate
Column
5 m XE 60 L-valine tert-butylamide
(0.2 mm diameter)
165° C., argon as CG (1 ml/min), FID
Retention times
R enantiomer: 4.3 min
S enantiomer: 4.6 min ItH2/ItMe2
Methyl (R/S)-2-methylsuccinate
Column
25 m Lipodex E (MACHEREY+NAGEL)
85° C., argon as CG (1 ml/min), FID
Retention times
S enantiomer: 11.67 min
R enantiomer: 12.23 min
Asymmetric Hydrogenation
Conditions
1 bar of $H_2$, 15 ml of MeOH, 25° C., 1 mmol of substrate, 0.01 mmol of catalyst (3);
AH: 93.1% ee of (S) product $t_{1/2}$=31 min
AMe: 97.5% ee of (S) product $t_{1/2}$=26 min

We claim:

1. A phospholane or diphospholane of the formula I

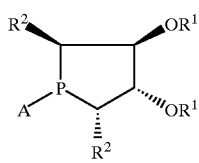

where
$R^1$ is H, $C_1$–$C_6$-alkyl, aryl, or alkylaryl,
$R^2$ is $C_1$–$C_6$-Alkyl, aryl, or alkylaryl,
A is either $R^1$ or

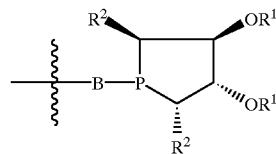

B is a linker having 1–5 carbon atoms between the two phosphorous atoms.

2. A phospholane as claimed in claim 1, wherein the substituents have the following meaning:
$R^1$ benzyl, methyl, tert-butyl, or together with the other substituent $R^1$, isopropylidene or benzylidene.

3. A diphospholane as claimed in claim 1, wherein the substituents have the following meaning:

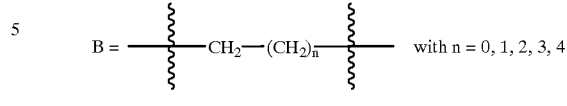

or

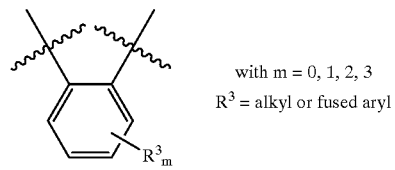

with m = 0, 1, 2, 3
$R^3$ = alkyl or fused aryl

4. A diphospholane as claimed in claim 3, wherein the substituents have the following meaning:
m=0, n=1.

5. A metal complex of a phospholane as claimed in claim 1 and a central atom selected from the group of Rh, Ru, Ir, Pd, Pt, Ni.

6. A metal complex as claimed in claim 5, wherein Rh or Ru is selected as central atom.

7. A metal complex as claimed in claim 6, wherein the phospholane or diphospholane is selected from those claimed in claims 2–4.

8. A process for hydrogenation, hydroformylation, hydrocyanation, allylic substitution, or isomerization of allylamines to enamines by using as a catalyst the metal complex of claim 5.

9. A process for the asymmetric hydrogenation of compounds by reacting the starting compounds which are to be hydrogenated with hydrogen in the presence of a metal complex as claimed in claim 5.

10. A process as claimed in claim 9, wherein the hydrogenation is carried out under a hydrogen pressure of from 1 to 2 bar.

* * * * *

UNITED STATES PATENT AND TRADEMARK OFFICE
CERTIFICATE OF CORRECTION

PATENT NO. : 6,043,396
DATED : March 28, 2000
INVENTOR(S) : Sturmer, et. al.

It is certified that error appears in the above-identified patent and that said Letters Patent is hereby corrected as shown below:

Column 9, claim 1, line 28, change "Alkyl" to --alkyl--.

Signed and Sealed this

Sixth Day of February, 2001

Attest:

Q. TODD DICKINSON

Attesting Officer     Director of Patents and Trademarks